United States Patent [19]

Yoshitome

[11] Patent Number: 5,751,782
[45] Date of Patent: May 12, 1998

[54] X-RAY COMPUTERIZED TOMOGRAPHY APPARATUS AND METHOD FOR CONTROLLING THE SAME

[75] Inventor: Eiji Yoshitome, Tokyo, Japan

[73] Assignee: GE Yokogawa Medical Systems, Limited, Tokyo, Japan

[21] Appl. No.: 636,797

[22] Filed: Apr. 22, 1996

[30] Foreign Application Priority Data

Jul. 10, 1995 [JP] Japan ................. 7-173065

[51] Int. Cl.$^6$ .................................. H05G 1/64
[52] U.S. Cl. ................................... 378/98.5
[58] Field of Search ................. 378/4, 21, 98.2, 378/98.4, 98.5, 98.11, 98 R

[56] References Cited

U.S. PATENT DOCUMENTS 5,357,550  10/1994  Asahina et al. ............ 378/98.5
5,463,666  10/1995  Eberhard et al. ............ 378/4

FOREIGN PATENT DOCUMENTS 026530  2/1990  Japan.

*Primary Examiner*—Don Wong
*Attorney, Agent, or Firm*—Moonray Kojima

[57] ABSTRACT

An X-ray computerized tomography apparatus having an X-ray tube or detector constantly rotated an around an object for acquiring data during specific phase segments of the motion of the object. A period h and a phase are detected from R waves of an electrocardiogram. Searching is then done through a table to provide delay time d, measuring time e, rotating time k (being an integer not a multiple of period h), and counts n corresponding to the period h to the expression below:

$$k=(h-e)/(1-M);$$

wherein M is ($0 \leq M < 1$), n is obtained as an integer greater than k/(h-k). In operation, while the tube or detector is continuously rotated over k, X-rays are emitted at d. Data is measured during e, at the end of which the emission of X-rays is stopped. This is repeated as often as n until image reconstruction is acquired.

6 Claims, 4 Drawing Sheets

5,751,782

X-RAY COMPUTERIZED TOMOGRAPHY APPARATUS AND METHOD FOR CONTROLLING THE SAME

BACKGROUND OF THE INVENTION

Japanese Patent Laid-Open No. Hei 2-6530 (1990) discloses an X-ray computerized tomography apparatus capable of collecting data only during predetermined phase segments of the rhythmically recurrent movements of the human heart. FIG. 4 is a timing chart showing the timings used by the disclosed apparatus to collect data about the diastole of the heart (i.e., dilatation of its cavities). Reference characters in the figure have the following meanings:

Reference character (a) indicates an electrocardiographic signal whose R waves are tapped to detect the period h and phase of the heart beat.

Reference character (b) denotes delay times d for determining a measurement start timing and measuring times e during which to measure data. Data measurement is started at the beginning of each diastolic phase of the heart following a delay time d from the onset of each R wave. Data is measured during the measuring time e so that the data is acquired only during each diastolic phase.

Reference character (c) represents a measuring angle θ. If the complete view necessary for reconstructing an image ranges from 0 to 360 degrees, a first measurement collects data initially on a view ranging from 270 to 360 degrees. The first measurement is followed by a second measurement which gathers data on a view ranging from 180 to 270 degrees. A third measurement acquires data on a view ranging from 90 to 180 degrees, and a fourth measurement obtains data on a view ranging from 0 to 90 degrees.

Reference character (d) indicates times τ1 through τ4 at which to start a rotary scan whereby an X-ray tube and a detector are rotated around an object under observation, as well as rotating times k and stop times. The rotary scan start timing τ1 is determined so that the time period corresponding to a first rotation from 270 to 360 degrees coincides with the measuring time of the first measurement. The rotary scan start timing τ2 is determined so that the time period corresponding to a second rotation from 180 to 270 degrees coincides with the measuring time of the second measurement. Likewise, the timing τ3 is determined so that the time period corresponding to a third rotation from 90 to 180 degrees coincides with the measuring time of the third measurement, and the timing τ4 is determined so that the time period corresponding to a fourth rotation from 0 to 90 degrees coincides with the measuring time of the fourth measurement.

The rotation of the X-ray tube and detector is stopped from the end of the first rotation until the start of the second rotation, from the end of the second rotation until the start of the third rotation, and from the end of the third rotation until the start of the fourth rotation.

The conventional X-ray CT apparatus outlined above is effective where the X-ray tube and detector are stopped after every rotation and then reversed in direction for another rotation. However, if the above method is applied to an X-ray CT apparatus that rotates continuously during operation, the need to stop the rotation after each rotating period as shown in FIG. 1 renders the apparatus inefficient.

SUMMARY OF THE INVENTION

The present invention relates to an X-ray computerized tomography (CT) apparatus and a method for controlling the same. More particularly, the invention relates to an X-ray CT apparatus and a method for controlling the same whereby, when the object to be scanned has a periodic motion, data is collected only during specific phase segments of the motion. The computerized tomography of the invention is effective in taking tomographic images of the heart during its diastolic phase or in dividing a single period of the heart movement into a plurality of phase segments which are imaged and displayed in cine.

It is an object of the present invention to provide an X-ray computerized tomography (CT) apparatus and a method for controlling the same such that, with an X-ray tube or a detector rotated continuously at a constant speed around the object to be scanned, data on the object is collected only during specific phase segments of the periodic motion of the object.

In carrying out the invention and according to a first aspect thereof, there is provided a control method for controlling an X-ray computerized tomography apparatus having at least one of an X-ray and a detector rotated around an object to be scanned in order to acquire data constituting a complete view necessary for reconstructing an image of the object. The method comprises the steps of: continuously rotating at least one of the X-ray tube and the detector over a time which is not an integer multiple of the period of the motion of the object; starting to measure data the moment a specific phase of the motion is reached; repeatedly measuring data constituting a view corresponding to a rotating angle representing a shorter measuring time than the period of the motion, until the data constituting the complete view necessary for reconstructing the image of the object is acquired; and generating a tomographic image of the object on the basis of the data thus acquired.

According to a second aspect of the invention, there is provided a control method for controlling an X-ray computerized tomography apparatus having at least one of an X-ray and a detector rotated around an object to be scanned in order to acquire data constituting a complete view necessary for reconstructing an image of the object. The method comprises the steps of:

continuously rotating at least one of the X-ray tube and the detector over a time which is not an integer multiple of the period of the motion of the object;

starting to measure data every time one of a plurality of phase segments during the period of the motion is reached; repeatedly measuring data constituting a view corresponding to a rotating angle representing each of the phase segments, until the data constituting the complete view necessary for reconstructing an image corresponding to each of the phase segments is acquired;

generating a tomographic image corresponding to each of the phase segments on the basis of the data thus acquired; and displaying in cine the tomographic images thus generated.

According to a third aspect of the invention, there is provided an X-ray computerized tomography apparatus having at least one of an X-ray and a detector rotated around an object to be scanned in order to acquire data constituting a complete view necessary for reconstructing an image of the object. The apparatus comprises: motion detecting means for detecting a period h and a phase of the motion of the object; measurement start timing controlling means for starting data measurement by use of the timing of a specific phase of the motion; measuring time setting means for setting a measuring time e in which to measure data, the measuring time being shorter than the period h; rotating time setting means for setting the rotating time of at least one of the X-ray tube and the detector on the basis of the period h and the measuring time e, the rotating time being other than an integer multiple of the period h; and data acquiring means for continuously rotating at least one of the X-ray tube and the detector over the rotating time, the data acquiring means further starting to measure data by use of the timing set by the measurement start timing controlling means, the data acquiring means further measuring repeatedly data constituting a view corresponding to a rotating angle reflecting the measuring time e, until the data constituting the complete view necessary for reconstructing the image of the object is acquired.

In a first preferred structure according to the invention, the rotating time setting means of the X-ray computerized tomography apparatus uses one of two formulas to set the rotating time, the formulas being defined as $$\text{rotating time}=(\text{period } h-\text{measuring time } e)/(1-M)$$

$$\text{rotating time}=(\text{period } h+\text{measuring time } e)/(1+M)$$

where M, which is at least 0 and less than 1, is a margin representing in rotation frequency the angle of the data measured in duplicate from a plurality of measurements conducted. The period h may be replaced by 1 divided by a cycle count, and the result is still the same.

In a second preferred structure according to the invention, the X-ray computerized tomography apparatus further comprises setting means for setting a plurality of pairs of a data measurement start timing and a measuring time each, whereby the data constituting the complete view necessary for reconstructing a plurality of images of the object is acquired during a single rotation of at least one of the X-ray tube and the detector.

In a third preferred structure according to the invention, the X-ray computerized tomography apparatus further comprises setting means for setting every measuring time in accordance with the formula defined as $$\text{measuring time } e=(\text{period } h-\text{nonmeasurable time } m)/b$$

where b stands for the number of phase segments and m for the time that exceeds a temporal window in which measurements are permitted even if R waves appear at irregular intervals. With this apparatus, each measurement start timing is delayed by the measuring time e. There are provided b pairs of a data measurement start timing and a measuring time each, and a plurality of reconstructed images of the object are displayed in cine.

With respect to the control method according to the first aspect of the invention, if the rotating time is set as a time other than an integer multiple of the period of the moving object to be scanned, the relation in phase between the period of the object's motion and the rotating time develops a discrepancy reflecting the difference in time therebetween. With at least either the X-ray tube or the detector rotated continuously, data measurement is started in a predetermined phase of the motion. The data is measured on a view corresponding to the rotating angle reflecting the measuring time. Measurement of the data is repeated as many times as the number given by dividing the rotating angle corresponding to the complete view necessary for reconstructing an image, by the angle corresponding to the phase discrepancy mentioned above. This permits acquisition of the data on the complete view for reconstructing the image of the object. In other words, the data on the complete view for reconstructing the image is acquired by carrying out data measurement in specific phase segments of the periodic motion of the object while the X-ray tube or detector is being rotated continuously at a constant speed.

The rotating time, measurement start timing, measuring time and measurement count may all be set manually by the operator. Alternatively, there may be provided beforehand a table (or a set of relational expressions) accommodating combinations of rotating times, measurement start timings, measuring times and measurement counts. The table allows the operator to set some parameters manually, and the remaining parameters are retrieved (or calculated) automatically. As another alternative, there may be provided in advance a table (or a set of relational expressions) accommodating combinations of periods, rotating times, measurement start timings, measuring times and measurement counts. This table allows the operator to set a period (or cycle count) manually, and the corresponding rotating time, measurement start timing, measuring time and measurement count are retrieved (or calculated) automatically. As a further alternative, the above table (or set of relational expressions) may be accompanied by a measuring instrument for measuring the period (or cycle count) of the object. In this case, the period (or cycle count) of the moving object is actually measured, and the measurement is used as the basis for retrieving (or calculating) the corresponding rotating time, measurement start timing, measuring time and measurement count.

By use of the control method according to the second aspect of the invention, one period of the motion of, say, the heart may be divided and imaged in a plurality of phase segments. The images thus taken may be observed in the form of an animation.

Phase segments may be set manually by the operator. Alternatively, there may be provided beforehand a table (or a set of relational expressions) accommodating combinations of phase segment counts and phase segments. The table allows the operator to set a desired phase segment count, and the corresponding phase segments are retrieved (or calculated) automatically. As another alternative, there may be provided in advance a table (or a set of relational expressions) accommodating combinations of periods and phase segments. This table allows the operator to set a desired period (or cycle count), and the corresponding phase segments are retrieved (or calculated) automatically. As a further alternative, the above table (or set of relational expressions) may be accompanied by a measuring instrument for measuring the period (or cycle count) of the object. In this case, the period (or cycle count) of the moving object is actually measured, and the measurement is used as the basis for retrieving (or calculating) the corresponding phase segments.

The X-ray CT apparatus according to the third aspect of the invention allows the control method of the first aspect to be implemented advantageously. That is, with the X-ray tube or detector rotated continuously at a constant speed, data is measured only during specific phase segments of the periodic motion of the object. This still permits acquisition of the data on the complete view necessary for reconstructing an image of the object.

With the X-ray CT apparatus in the first preferred structure according to the invention, the expression below defines the discrepancy angle $\phi$ representing the angle of discrepancy per rotation due to the difference in time between the period h of the object's motion and the rotating time:

$$\phi=\text{1period } h-\text{rotating time/rotating time} \qquad (1)$$

If it is assumed that the discrepancy angle $\phi$ represents the measuring time, that there are n measurements conducted and that the complete view necessary for reconstructing an image of the object is equivalent to a complete rotation (full scan), the following relation should hold:

$$\phi \times \text{measurement count } n > 1 \qquad (1)$$

Given the expression (1) above, the following relation should hold:

$$|\text{period } h - \text{rotating time}| \times \text{measurement count } n/\text{rotating time} \geq 1 \qquad (2)$$

Where the relation (2) above is satisfied, the data on the complete view necessary for reconstructing the view is acquired.

If e stands for the measuring time during a rotation, then the following expression provides a measured data angle $\Theta$ per rotation, i.e., an angle representing in units of rotations the angle of the data acquired by measurements during a single rotation:

$$\Theta = \text{measuring time } e/\text{rotating time} \qquad (3)$$

If the value $\Theta$ is greater than $\phi$ mentioned above, a plurality of measurements conducted provide measured data partially in duplicate. Thus the equation below when applied gives the margin M representing in rotations the angle of the data measured in duplicate from a plurality of measurements performed:

$$M = \Theta - \phi$$

Given the expressions (1) and (3) above, the margin M is determined as $$M = \text{measuring time } e/\text{rotating time} - |\text{period } h - \text{rotating time}|/\text{rotating time} \qquad (4)$$

The margin M ($0 \leq M < 1$) is set as desired by the operator or is set by default.- Whereas data losses resulting from irregular periods can be compensated by data interpolation calculations, the losses may be minimized if the margin M is set to be greater than 0. On the other hand, if the margin M is set as 0, data acquisition is terminated quickly.

On the assumption that the period h is greater than the rotating time, the expression (4) above may be converted as follows:

$$\text{rotating time} = (\text{period } h - \text{measuring time } e)/(1-M) \qquad (5)$$

Here, the relation (2) is converted to:

$$\text{measurement count } n \geq \text{rotating time}/(\text{period } h - \text{rotating time}) \qquad (6)$$

Thus with the X-ray tube or detector rotated continuously at a constant speed, data is measured only during specific phase segments of the periodic motion of the object, until the data on the complete view necessary for reconstructing an image of the object (i.e., full scan) is acquired.

If it is assumed that the period h is shorter than the rotating time, the expression (4) above may be converted as follows:

$$\text{rotating time} = (\text{period } h + \text{measuring time } e)/(1+M) \qquad (7)$$

Here, the relation (2) is converted to:

$$\text{measurement count } n \geq \text{rotating time}/(\text{rotating time} - \text{period } h) \qquad (8)$$

If the complete view necessary for reconstructing an image of the object is equivalent to a half rotation (i.e., half scan), the relation (2) is converted:

$$|\text{period } h - \text{rotating time}| \times \text{measurement count } n/\text{rotating time} \geq (0.5 + f) \qquad (9)$$

where, f represents the angle ratio of a fan-beam spread angle to one complete rotation. Thus if the period h is assumed to be longer than the rotating time, the following relation holds:

$$\text{measurement count } n \geq (0.5+f) \times \text{rotating time}/(\text{period } h - \text{rotating time}) \qquad (10)$$

If the period h is assumed to be shorter than the rotating time, the following relation holds:

$$\text{measurement count } n \geq (0.5+f) \times \text{rotating time}/(\text{rotating time} - \text{period } h) \qquad (11)$$

With the X-ray CT apparatus in the second preferred structure according to the invention, it is possible concurrently to take a tomographic image of, say, the heart during its diastolic phase as well as a tomographic image during its contractional phase.

The X-ray CT apparatus in the third preferred structure according to the invention allows the motion of a single period of, say, the heart to be divided into a plurality of phase segments and imaged for each. The images thus taken may be observed in the form of an animation.

These and other objects, features and advantages of the invention will become more apparent upon a reading of the following description and appended drawings.

DESCRIPTION OF THE PREFERRED EMBODIMENTS

Preferred embodiments of the invention will now be described in detail with reference to the accompanying drawings. It is to be noted that these embodiments are for illustrative purposes only and are not limitative of the present invention.

First Embodiment

Figure 1:
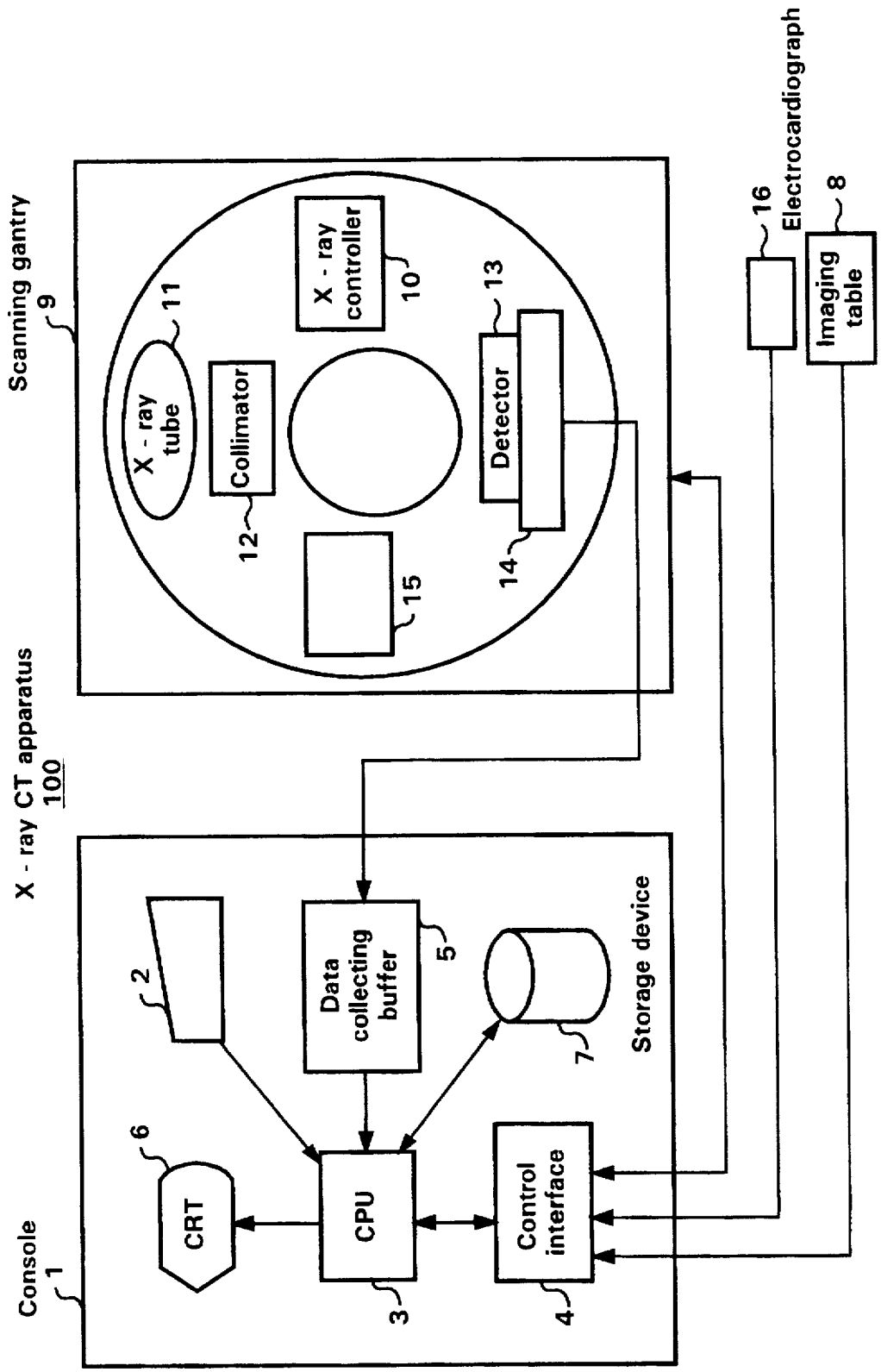
FIG. 1 is a block diagram of an X-ray computerized tomography (CT) apparatus practiced as a first embodiment of the invention.

FIG. 1 is a block diagram of an X-ray CT apparatus 100 practiced as the first embodiment of the invention. The X-ray CT apparatus comprises a console 1, an imaging table 8, a scanning gantry 9 and an electrocardiograph 16.

The console 1 includes an input device 2 that receives the operator's instructions and data, a central processing unit (CPU) 3 that executes image reconstruction processing and other computations, a control interface 4 which exchanges control signals with the imaging table 8 and scanning gantry 9 and which receives electrocardiographic signals from the electrocardiograph 16, a data collecting buffer 5 that accommodates data acquired by the scanning gantry 9, a CRT 6 that displays an image reconstructed from the above data, and a storage device 7 that stores programs and data.

The imaging table 8 carries the object to be scanned and moves it in the axial direction of its body.

The scanning gantry 9 comprises an X-ray controller 10, an X-ray tube 11, a collimator 12, a detector 13, a data collecting part 14, and a rotation controller 15 that controls the rotation of the X-ray tube or the like around the body axis of the object. A slip ring arrangement may be used to let the X-ray tube 11 or the like rotate continuously.

The X-ray controller 10 has the ability to turn on and off X-ray irradiation.

The rotation controller 15 has a servo motor and an encoder. For each angular position detected by the encoder, the controller 15 generates a trigger signal by which to collect view data with respect to that angular position.

The integral time of the data collecting part 14 may be changed using some of the trigger signals above.

The electrocardiograph 16 outputs electrocardiographic signals of the object under observation.

Figure 2:
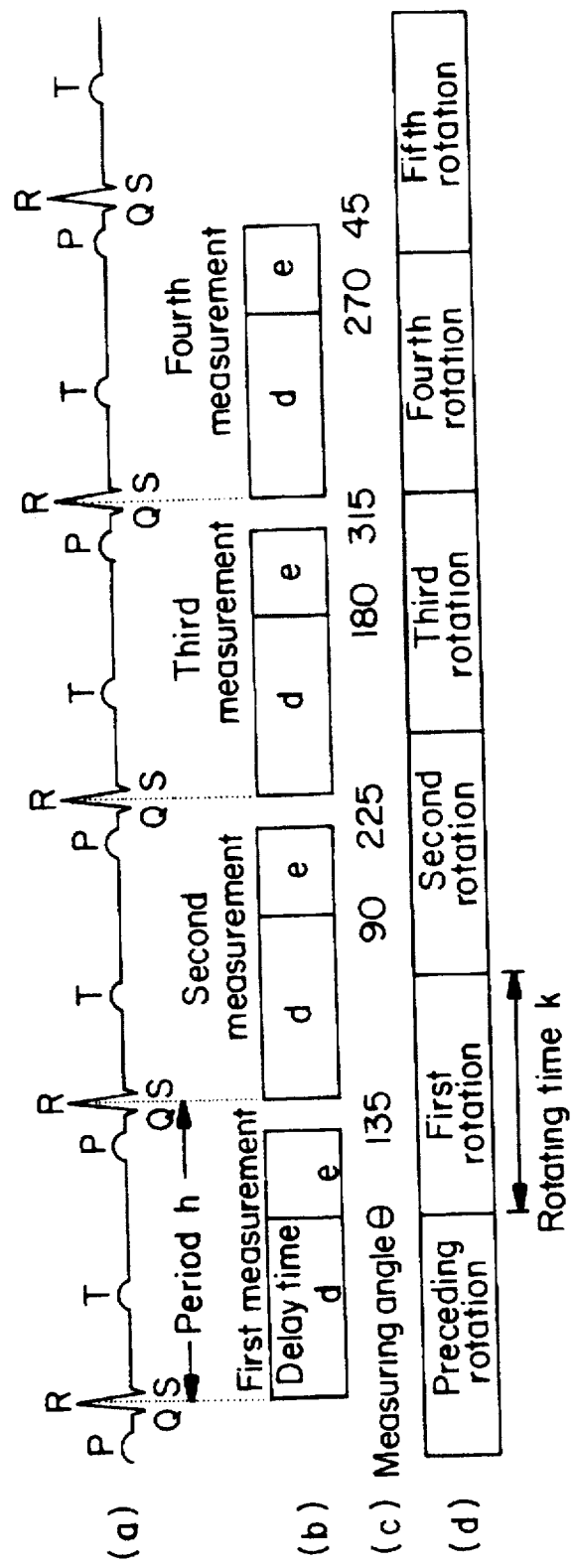
FIG. 2 is a timing chart in effect when the first embodiment is in operation.

FIG. 2 is a timing chart in effect when the X-ray CT apparatus 100 is used to collect data only about the diastolic phase of the heart.

When the operator designates "single phase mode" from the input device 2, the CPU 3 detects the period h and phase from R waves in the electrocardiographic signal indicated by reference character (a) in FIG. 2. It is assumed here that the period h is one second.

The CPU 3 then searches through a table accommodating combinations of periods, delay times, measuring times, measurement counts and rotating times, the table being stored beforehand in the storage device 7. In so doing, the CPU 3 retrieves the delay time d, measuring time e, rotating time k and measurement count n corresponding to the detected period h. It is assumed here that given the period h of 1 second, what is retrieved from the table are a delay time d of 600 ms, a measuring time e of 300 ms, a rotating time k of 800 ms and a measurement count n of 4.

The combinations of periods, delay times and measuring times for collecting data about the diastolic phase of the heart are empirically known. The rotating time is calculated by use of the following formula (the margin M for measurement is assumed to have been set to ⅛):

rotating time=(period−measuring time)/(1−⅛)

The measurement count is obtained as a minimum integer not smaller than: rotating time/(period−rotating time).

When the operator inputs a scan instruction from the input device 2, the CPU 3 causes the X-ray tube 11 or the like to be rotated continuously at a rotating speed of one rotation per rotating time k, as indicated by reference character (d) in FIG. 2. As denoted by reference character (b) in FIG. 2, X-ray irradiation is started the delay time d after the onset of each R wave. Data is measured during the measuring time e, at the end of which X-ray irradiation is stopped. The process is repeated as many times as the measurement count n. This makes it possible, as indicated by reference character (c) in FIG. 2, to measure data on a view ranging from 0 to 135 degrees of measuring angle θ in the first measurement, on a view ranging from 90 to 225 degrees of measuring angle θ in the second measurement, on a view ranging from 180 to 315 degrees of measuring angle θ in the third measurement, and on a view ranging from 270 to 45 degrees of measuring angle θ in the fourth measurement. That is, the data on the 360-degree view necessary for reconstructing a full-scan image of the object is collected with a margin of 45 degrees.

Using the data thus collected, the CPU 3 performs image reconstruction calculations to generate a tomographic image. At this point, the data measured in duplicate from a plurality of measurements is either averaged for use, or is processed so that only the data from one measurement is used. The lost data is interpolated by utilizing the data collected in the opposite direction or from an adjacent view.

Finally, the CPU 3 causes the CRT 6 to display the tomographic image thus generated.

As described, the X-ray CT apparatus practiced as the first embodiment allows data to be measured only during the diastolic phase of the heart while rotating the X-ray tube 11 or the like at a constant speed, until all data on the complete view necessary for reconstructing an image of the object is acquired. This permits advantageous acquisition of a tomographic image of the heart in its diastolic phase.

The timing chart in FIG. 2 shows measurement start timings being taken by detecting an R wave for each measurement. Alternatively, where the fluctuation in the period h is negligible, a first R wave alone may be detected and used as the basis for determining measurement start timings for use in the first through the n-th measurement.

Although FIG. 2 is a timing chart for acquiring a tomographic image of the heart in its diastolic phase, tomographic images of other phase segments may also be obtained by changing some parameters such as the delay time and measuring time.

The first embodiment is shown generating trigger signals by which to acquire data on the views corresponding to different angular positions. Alternatively, trigger signals may be generated to obtain data on the views corresponding to different points in time. In the alternative case, the number of views and their angle ranges for image reconstruction need only be changed in accordance with the rotating time k.

Second Embodiment

An X-ray CT apparatus practiced as the second embodiment of the invention is identical in constitution to the first embodiment of FIG. 1.

Figure 3:
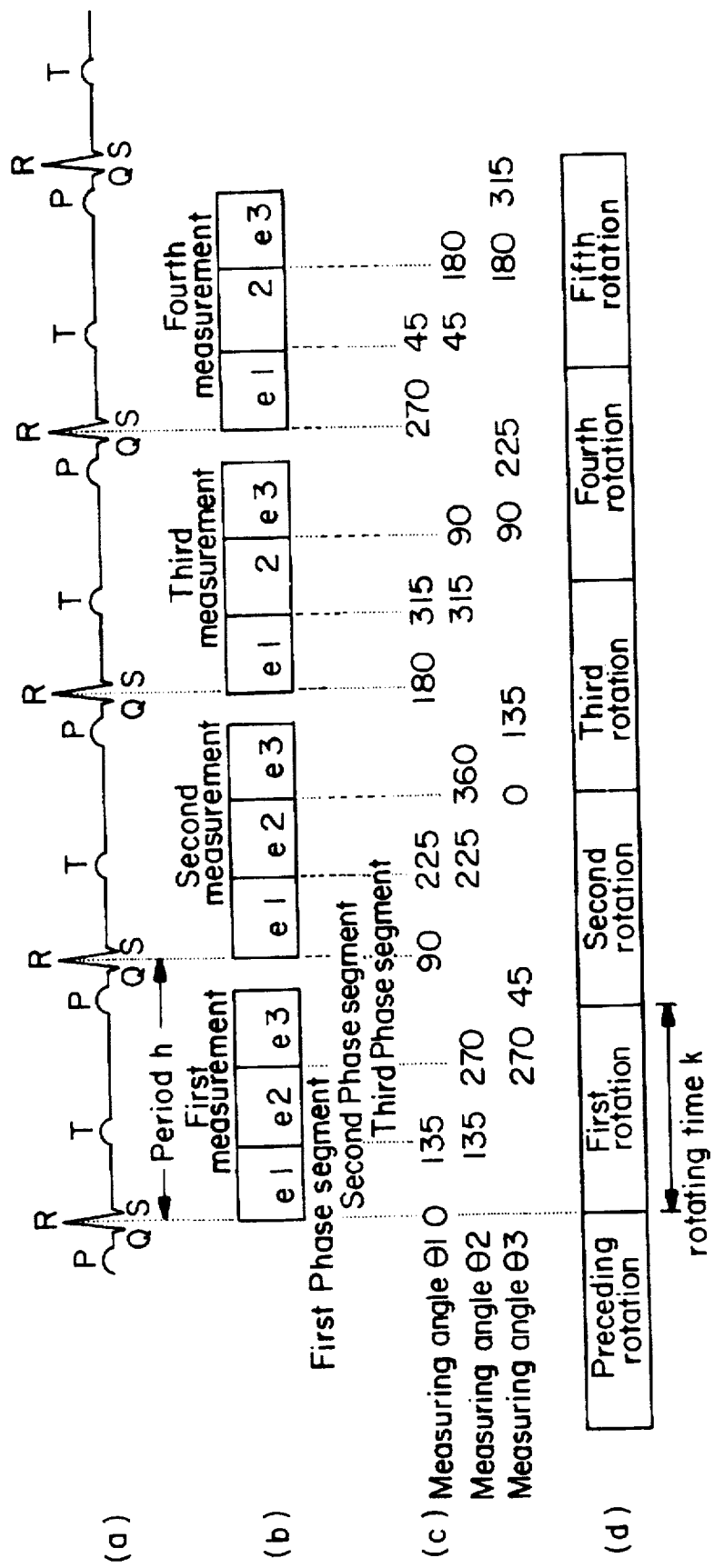
FIG. 3 is a timing chart in effect when an X-ray CT apparatus practiced as a second embodiment of the invention is in operation.
Figure 4:
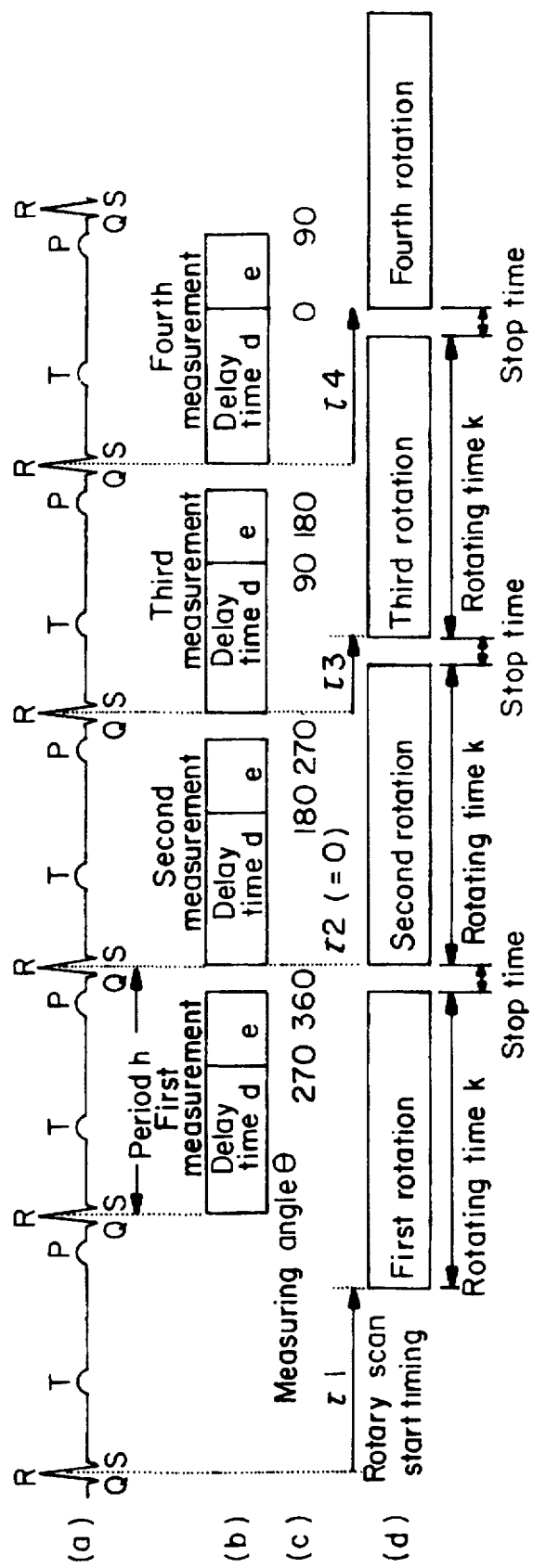
FIG. 4 is a timing chart that applies to a conventional X-ray CT apparatus.

FIG. 3 is a timing chart in effect when the second embodiment is operated to divide one period of the heart into three phase segments for imaging.

When the operator designates "multi-phase mode" and a phase segment count b from the input device 2, the CPU 3 detects the period h and phase from R waves in the electrocardiographic signal indicated by reference character (a) in FIG. 3. It is assumed here that the input phase segment count b is 3 and that the detected phase h is one second.

The CPU 3 then searches through a table accommodating combinations of periods, delay times and remaining times, the table being stored beforehand in the storage device 7. In so doing, the CPU 3 retrieves the delay time and remaining time corresponding to the detected period h. The delay time lasts from the onset of an R wave until the start of measurement. The remaining time is a time from the end of measurement up to the onset of the next R wave. Adding up the delay time and remaining time constitutes a nonmeasurable time m. Although the delay time and remaining time may be zero each, irregularities in the period h can be better absorbed if at least one of these times is not zero. The combinations of periods, delay times and remaining times for collecting data about the heart are empirically known. It is assumed here that given the period h of 1 second, what is retrieved from the table are a delay time d of 0 ms and a remaining time of 100 ms.

The CPU 3 calculates the measuring time and rotating time by use of the following formulas (the margin M for measurement is assumed to have been set to ⅛):

measuring time=(period−delay time−remaining time)/phase segment count n rotating time=(period−measuring time)/(1−⅛)

The measurement count is obtained as a minimum integer not smaller than: rotating time/(period−rotating time). In this example, the calculations above are assumed to have produced measuring times (e1, e2, e3) of 300 ms each, a rotating time k of 800 ms and a measurement count n of 4.

The operator then inputs a scan instruction from the input device 2. In response, the CPU 3 causes the X-ray tube 11 or the like to be rotated continuously at a rotating speed of one rotation per rotating time k, as indicated by reference character (d) in FIG. 3. As denoted by reference character (b) in FIG. 3, X-ray irradiation is started the delay time d (0 in this case) after the onset of each R wave. Data is measured during the measuring times e1, e2 and e3 for the first, the second and the third phase segment, respectively. X-ray irradiation is stopped at the end of data measurement over the measuring time e3 for the third phase segment. The process is repeated as many times as the measurement count n. This makes it possible, as indicated by reference character (c) in FIG. 3, to measure data in the first measurement on a view ranging from 0 to 135 degrees of measuring angle θ1 for the first phase segment, on a view ranging from 135 to 270 degrees of measuring angle θ2 for the second phase segment, and on a view ranging from 270 to 45 degrees of measuring angle θ3 for the third phase segment. In the second measurement, data is measured on a view ranging from 90 to 225 degrees of measuring angle θ1 for the first phase segment, on a view ranging from 225 to 360 degrees of measuring angle θ2 for the second phase segment, and on a view ranging from 0 to 135 degrees of measuring angle θ3 for the third phase segment. In the third measurement, data is measured on a view ranging from 180 to 315 degrees of measuring angle θ1 for the first phase segment, on a view ranging from 315 to 90 degrees of measuring angle θ2 for the second phase segment, and on a view ranging from 90 to 225 degrees of measuring angle θ3 for the third phase segment. In the fourth measurement, data is measured on a view ranging from 270 to 45 degrees of measuring angle θ1 for the first phase segment, on a view ranging from 45 to 180 degrees of measuring angle θ2 for the second phase segment, and on a view ranging from 180 to 315 degrees of measuring angle θ3 for the third phase segment. That is, the data on the 360-degree view necessary for reconstructing a full-scan image for each of the first through the third phase segment is collected with a margin of 45 degrees.

Using the data thus collected, the CPU 3 performs image reconstruction calculations to generate a tomographic image for each of the first through the third phase segment. The tomographic images thus generated are displayed in cine on the CRT 6 in the order of their corresponding phase segments.

As described, the X-ray CT apparatus practiced as the second embodiment of the invention allows the motion of a single period of the heart to be divided into a plurality of phase segments and imaged for each while the X-ray tube or the like is rotated continuously at a constant speed. The images thus taken are observed in the form of an animation.

Other Embodiments

The invention also applies to a helical scan setup where data is collected by having at least either the X-ray tube or the detector rotated around the object to be scanned while the object is moved linearly relative to the X-ray tube and detector. In this setup, multiple sliced images for a specific phase segment (the diastolic phase of the heart, for example) are obtained either by reconstructing them without regard to negligible spatial discrepancies in data (such discrepancies are negligible when the speed of the linear movement is relatively low given the complexity of the structure of the object), or by reconstructing the images through spatial data interpolation (such interpolation is needed when the speed of the linear movement is relatively high in view of the complexity of the structure of the object). Where the above arrangements are made, the entire target organ may be imaged with a single holding of the breath on the part of the patient. The interpolation above may typically be linear interpolation of the data collected one or a half rotation apart.

As described and according to the invention, the X-ray CT apparatus and the method for controlling the same allow data to be collected only during specific phase segments of the periodic motion of the object under observation while continuously rotating the X-ray tube or detector at a constant speed.

According to the inventive X-ray CT apparatus and the method for controlling the same, the motion of the object in a single period is divided into a plurality of segments and imaged for each while the detector is continuously rotated at a constant speed. The images of the object thus acquired are observed in the form of an animation.

As many apparently different embodiments of this invention may be made without departing from the spirit and scope thereof, it is to be understood that the invention is not limited to the specific embodiments thereof except as defined in the appended claims.

What is claimed is:

1. A control method for controlling an X-ray computerized tomography apparatus having at least one of an X-ray tube and a detector rotated around an object to be scanned in order to acquire data constituting a complete view necessary for reconstructing an image of said object, said method comprising the steps of:

continuously rotating at least one of said X-ray tube and said detector over a time which is not an integer multiple of the period of the motion of said object;

starting to measure data the moment a specific phase of said motion is reached;

repeatedly measuring data constituting a view corresponding to a rotation angle representing a shorter measuring time than said period of said motion, until the data constituting the complete view necessary for reconstructing said image of said object is acquired; and generating a tomographic image of said object on the basis of the data thus acquired.

2. A control method for controlling an X-ray computerized tomography apparatus having at least one of an X-ray tube and a detector rotated around an object to be scanned in order to acquire data constituting a complete view necessary for reconstructing an image of said object, said method comprising the steps of:

continuously rotating at least one of said X-ray tube and said detector over a time which is not an integer multiple of the period of the motion of said object;

starting to measure data every time one of a plurality of phase segments during said period of said motion is reached;

repeatedly measuring data constituting a view corresponding to a rotation angle representing each of said phase segments, until the data constituting the complete view necessary for reconstructing an image corresponding to each of said phase segments is acquired;

generating a tomographic image corresponding to each of said phase segments on the basis of the data thus acquired; and displaying in cine the tomographic images thus generated.

3. An X-ray computerized tomography apparatus having at least one of an X-ray tube and a detector rotated around an object to be scanned in order to acquire data constituting a complete view necessary for reconstructing an image of said object, the apparatus comprising:

motion detecting means for detecting a period h and a phase of the motion of said object;

measurement start timing controlling means for starting data measurement by use of the timing of a specific phase of said motion;

measuring time setting means for setting a measuring time e in which to measure data, said measuring time being shorter than said period h;

rotating time setting means for setting the rotating time of at least one of said X-ray tube and said detector on the basis of said period h and said measuring time e, said rotating time being other than an integer multiple of said period h; and data acquiring means for continuously rotating at least one of said X-ray tube and said detector over said rotating time, said data acquiring means further starting to measure data by use of the timing set by said measurement start timing controlling means, said data acquiring means further measuring repeatedly data constituting a view corresponding to a rotation angle reflecting said measuring time e, until the data constituting the complete view necessary for reconstructing said image of said object is acquired.

4. An X-ray computerized tomography apparatus according to claim 3, wherein said rotating time setting means uses one of two formulas to set said rotating time, said formulas being defined as rotating time=(period $h$−measuring time $e$)/(1−$M$)

rotating time=(period $h$+measuring time $e$)/(1+$M$)

where M, which is at least 0 and less than 1, is a margin representing in rotation frequency the angle of the data measured in duplicate from a plurality of measurements conducted.

5. An X-ray computerized tomography apparatus according to claim 3 or 4, further comprising setting means for setting a plurality of pairs of a data measurement start timing and a measuring time each, whereby the data constituting the complete view necessary for reconstructing a plurality of images of said object is acquired during a single rotation of at least one of said X-ray tube and said detector.

6. An X-ray computerized tomography apparatus according to claim 5, further comprising setting means for setting every measuring time in accordance with the formula defined as measuring time $e$=(period $h$−nonmeasurable time $m$)/$b$ where b stands for the number of phase segments and m for the time in which no measurement takes place, wherein each measurement start timing is delayed by said measuring time e, wherein there are provided b pairs of a data measurement start timing and a measuring time each, and wherein a plurality of reconstructed images of said object are displayed in cine.

* * * * *